(12) United States Patent
Yang

(10) Patent No.: US 8,399,253 B2
(45) Date of Patent: *Mar. 19, 2013

(54) PROLIFERATION CULTURE METHODS USING MICRO-SCAFFOLDS FOR REGULATIONS OF CELL-TO-CELL SIGNALS

(76) Inventor: Hyunjin Yang, Seoul (KR)

( * ) Notice: Subject to any disclaimer, the term of this patent is extended or adjusted under 35 U.S.C. 154(b) by 441 days.

This patent is subject to a terminal disclaimer.

(21) Appl. No.: 12/598,032

(22) PCT Filed: Apr. 28, 2007

(86) PCT No.: PCT/KR2007/002108
§ 371 (c)(1),
(2), (4) Date: Mar. 31, 2010

(87) PCT Pub. No.: WO2008/133362
PCT Pub. Date: Nov. 6, 2008

(65) Prior Publication Data
US 2010/0178701 A1  Jul. 15, 2010

(51) Int. Cl.
*C12N 5/02* (2006.01)
(52) U.S. Cl. ........ 435/403; 422/533; 422/548; 422/550; 422/546
(58) Field of Classification Search ................ 422/533, 422/548, 550, 546; 435/403
See application file for complete search history.

(56) References Cited

U.S. PATENT DOCUMENTS
2003/0093034 A1 * 5/2003 Chang et al. .................. 604/190

FOREIGN PATENT DOCUMENTS
JP       05091872 A  *  4/1993

OTHER PUBLICATIONS

Machine Translation of JP-05091872 downloaded from the JPO May 22, 2012.*

* cited by examiner

*Primary Examiner* — Susan Hanley
*Assistant Examiner* — Nghi Nguyen
(74) *Attorney, Agent, or Firm* — John K. Park; Park Law Firm

(57) ABSTRACT

A three-dimensional cell culture method for increasing cell proliferation efficiency by suitably regulating the proliferation-inducing and proliferation-inhibitory signals between cells is provided. The method includes repeatedly performing any one or both of the following processes a) and b) so as to regulate proliferation-inducing and proliferation-inhibitory signals between the cells: a) a process of gradually adding the micro-scaffolds, in which a small amount of the micro-scaffolds are used in an initial stage in order to maintain a suitable distance between the cells, and the amount of the micro-scaffolds is then increased slowly according to cell proliferation rate; and b) a periodic shaking process, in which shaking is performed in order to separate connected cells from each other by a physical force, after the cells are incubated for more than a given period of time.

1 Claim, 8 Drawing Sheets

PROLIFERATION CULTURE METHODS USING MICRO-SCAFFOLDS FOR REGULATIONS OF CELL-TO-CELL SIGNALS

TECHNICAL FIELD

The present invention relates to a method for three-dimensional Iy culturing cells using micro-scaffolds having surface areas allowing the adhesion and proliferation of the cells.

The present invention relates to a three-dimensional cell culture method for increasing cell proliferation efficiency by suitably regulating proliferation-inducing and proliferation-inhibitory signals between cells, which are the greatest variables in proliferation efficiency, the method comprising separating stromal stem cells from fat tissues, allowing the stromal stem cells to proliferate into desired cell types and, if necessary, allowing the proliferated cells to differentiate.

BACKGROUND ART

As a result of stem cell studies, which have recently been rapidly advanced, it has become possible to separate stromal stem cells from fat tissues and allow the stem cells to proliferate and differentiate into desired cell types. However, there are many problems in the practical application of stem cell culture, a large number of expensive systems and facilities, researcher staffs and expensive suppliers are necessary.

Particularly, when the cell culture process is carried out without thorough preparation, contamination with bacteria in air can occur, leading to the failure of the entire process, and there will be various failure factors, including a failure caused by the mistake of research staffs. For this reason, to obtain successful study results, enormous equipment investment and the training of research staffs are required.

For example, clean rooms or clean benches, in which air flows downward, are required for reducing contamination with bacteria in air. Also, attendant facilities, including disinfection equipment for disinfecting various containers, air cleaners, and suction units, are required. Moreover, research staffs should necessarily be trained through long-term exercise in order for the research staffs to use such facilities correctly and not to be contaminated during complicated processes.

Meanwhile, conditions for inducing cell proliferation include many chemical environments, but some of which are not yet clearly understood. The inhibition of cell proliferation is also greatly influenced by the environment thereof, and in this case, it seems that there are many principles, which are not yet established. For example, there is an experimental report that, when germs are present at a density of more than $10^6$ germs per $cm^2$ of human tissue, the proliferation thereof in the human body will be accelerated to cause inflections, but the precise mechanism thereof is not yet established. In the case of the culture of general cells, there are reports that, when more than a given number of cells are somewhat clustered, cell proliferation signals occur to induce the exponential proliferation of the cells; however, precise materials and principles for the cell proliferation are not yet established, except that the cell proliferation is possible in water-soluble materials and conductive materials.

For the inhibition of cell proliferation, various environments have also been reported. Among them, a clear principle is the contact inhibition phenomenon that, when cells are present attached laterally, the cells no longer proliferate in that direction.

In these points of view, the prior culture methods for cell proliferation have advantages and disadvantages as follows.

[Plate Culture]

A traditional cell culture method is a plate culture method of inducing cell division on a plate in medium. In this method, specific cells are spread and attached to the plate and allowed to grow and proliferate toward their surrounding regions. Then, as the cells reach saturation density, the cells are isolated from the structure having the cells attached thereto, using an enzyme such as trypsin. The resulting cell suspension is centrifuged, and the cells deposited on the bottom of the centrifuge are collected, and suspended in a sufficient amount of phosphate buffer saline (PBS) to wash out the enzyme. The cell suspension is centrifuged again to deposit the cells on the bottom of the centrifuge. After this process is repeated several times, the cells are suspended in medium and seeded (loaded) onto a fresh plate. As the cells grow to saturation, the same process as described is repeated. In this way, an exponential increase in the number of the cells can be achieved.

This method has a limitation on proliferation rate, because cell proliferation occurs only at the periphery of cell colonies, cells surrounded by other cells do not proliferate, and thus substantial cell proliferation occurs only at the outer edges of cell colonies. For this reason, the principle of plate culture is to maximize the number of proliferating cells by increasing the number of cell colonies.

In this case, the cell adhesion surface is the bottom or wall of a container, and only a single cell layer is formed without the deposition of cells. Thus, the plate culture is also called "mono-layer culture".

[Three-Dimensional Culture in the Absence of Scaffold]

This is a culture method for solving the limitation of the plate culture by controlling proliferation conditions in a state in which cells are suspended in liquid or on gel. In this method, a flow of liquid may also be controlled for proper conditions. Conceptually, this culture method is three-dimensional culture, shows no cell-to-cell contact inhibition and has much more chances than those of the plate culture with respect to the direction of proliferation of cells. However, the recognition of proliferation signals between cells and the division rate of cells are reduced. Thus, this method has limitations on the kind of cells and culture conditions in order to substantially increase proliferation rate.

[Three-Dimensional Culture Using Scaffold Other than Micro-Scaffolds]

A scaffold is a structure on which cells can adhere and grow and is a material, which serves to secure a space for cell growth and, at the same time, control the shape of cell colonies, because the shape of cell colonies depends on the scaffold. Culture using the scaffold is called "three-dimensional culture" in the sense that it has a cell adhesion surface significantly larger than that of the plate culture and that it can form a layered structure, because cells can grow not only in a planar direction, but also in upward and downward directions.

Scaffolds for use in three-dimensional culture are mostly solids, but in some cases, may also be gelatin-like materials which exist in an intermediate state between liquid and solid.

The scaffolds have a porous structure, which allows the movement of most of media and has a maximized surface area for cells adhesion. These scaffolds are in the shape of a sponge-like disc, a block or a sphere.

These scaffolds have a structure in which cell adhesion surfaces are layered or curved into a complicated shape so as to maximize the cell adhesion surface area. However, because cells can grow through the scaffolds, they can hardly grow inside of the scaffold, and thus reach saturation. For this reason, the cells can further proliferate only after a process of separating the cells from the scaffold after saturation and seeding the separated cells onto a fresh scaffold. Thus, a process of separating and washing cells are necessarily performed as in the plate culture.

[Three-Dimensional Culture Using Micro-Scaffolds]

Although this culture method employs solid powder, it is considered that the powder particles are saturated while they aggregate together by cells. For cell dispersion and seeding for increasing the proliferation of cells, a process of separating cells using an enzyme such as trypsin should generally be performed as before. This culture method shows an increase in proliferation rate and efficiency compared to other prior methods, but has problems in that the cell separation and seeding step still requires a given amount of effort and time, and cell viability is reduced due to chemical separation.

[Suspension Culture Using Scaffold]

In this culture method, cells together with a given amount of scaffolds are continuously suspended to induce cell adhesion to the scaffolds. However, as the scaffold particles are saturated due to the adhesion of cells, the cells no longer proliferate. Thus, the number of particles, on which cell proliferation occurs, increases with the passage of time, but the rate of saturated particles also increases, leading to a decrease in the total amount of proliferation inhibition. In this method, it is easy to maintain cells at constant density by regulating only media; however, because this method is dynamic, the proliferation-inducing signal exchange between cells does not occur and there is no advantage in a state in which cells adhere to a static surface.

[Static Culture Using Scaffold]

An example of static culture is a method comprising seeding cells onto a sufficient amount of scaffolds and forming a vortex flow in the medium to move non-adhered cells so as to increase the chance to adhere to the scaffolds. However, cells are partially saturated to increase the ratio of cells surrounded by the same cells, thus increasing the amount of cell-to-cell contact inhibition and reducing the amount of cell proliferation signals due to an excessively low cell density in an initial state.

[Initial Shaking and Static Culture Using Scaffold]

In this culture method, the amount of cell-to-cell contact inhibition can be minimized by seeding cells onto a sufficient amount of scaffolds and shaking the medium at a suitable point of time only in an initial stage. However, the amount of proliferation-inducing signals between cells is also small due to an excessively low cell density in the initial stage. Also, cells are chemically separated, a process of adding an exponential number of scaffolds is not adopted, and thus a chemical cell separation process is performed for dispersion and seeding onto fresh scaffolds having no cells. However, when the addition of an exponential amount of scaffolds is not performed, a large amount of scaffolds should be used in an initial stage. For this reason, in this method, the penetration of medium into the scaffolds can become difficult from the initial culture stage to reduce the efficiency of the initial culture stage, thus making it difficult to maintain stem cells.

DISCLOSURE

Technical Problem

The present invention has been made in order to solve the above-described problems occurring in the prior art, and it is an object of the present invention to provide a cell culture method for increasing cell proliferation efficiency, the method comprising: properly using an environment where cell proliferation is accelerated by cell-to-cell signals or interactions; minimizing the phenomenon that, when proliferated cells adhere to each other, proliferation-inhibitory signals will increase to reduce the relative ratio of an area where cells can proliferate; and performing intercellular separation at a suitable point of time using physical force instead of using a chemical method, which is known to have a possibility of causing gene mutation.

Another object of the present invention is to provide a cell culture method, which can reduce the economic burden required for experiments by simplifying complicated culture processes and various systems and instruments, makes it possible to achieve advanced studies even in small-scale systems, and enables reliable research results to be obtained.

Technical Solution

To achieve the above objects, the present invention provides a three-dimensional cell culture method for increasing cell proliferation efficiency, the method employing a micro-scaffold (or micro-beads) in a medium and comprising: performing either a cell culture method comprising periodically repeating a static status and the moving status (that is, shaking, rolling, stirring, whirling, rocking, mixing, blending, rotation or the like) of the scaffolds, or a cell culture method comprising slowly increasing the amount of the scaffold, in which the cell culture methods are simultaneously or individually carried out; properly using an environment where cell proliferation is accelerated by cell-to-cell signals or interactions; minimizing the phenomenon that, when proliferated cells adhere to each other, proliferation-inhibitory signals will increase to reduce the relative ratio of an area where cells can proliferate; and performing intercellular separation at a suitable point of time using physical force instead of using a chemical method, which is known to have a possibility of causing gene mutation.

According to one aspect of the present invention, there is provided a method for culturing cells using a syringe, the method comprising "—a pretreatment step of extracting cells with a syringe, the piston of which can be opened and closed, and then centrifuging and washing the collected cells so as to be suitable for proliferation; a micro-scaffold-adhering step of opening the piston of the syringe, placing medium and micro-scaffolds into the syringe, adhering the cells and the micro-scaffolds to each other in a state suspended in the medium, and precipitating the cells adhered to the micro-scaffolds; a cell culture step of culturing the cells in a state in which the piston is opened; a proliferation step of, after a given time of cell culture, adding an additional medium and micro-scaffolds through the piston passage, and then subjecting the contents of the syringe to a moving, shaking, rolling, stirring, whirling, rocking, mixing, blending or rotation process; and a proliferation-repeating step of periodically repeating the proliferation step.

As described above, the present invention relates to the method for the three-dimensional culture of stem cells, which is characterized in that it shows a high increase in cell number and a high culture rate and has safety.

In the above method of the present invention, the pretreatment step is a pre-culture treatment comprising extracting cells and isolating the cells by treatment with collagenase, followed by a centrifugation process, a byproduct removal process and a washing process with PBS or like.

The micro-scaffold-adhering step is a step of mixing the cells with solid micro-scaffolds, on which the cells can adhere and grow, and precipitating the cells adhered to the micro-scaffolds in medium. Through this step, the entire surface of each of the micro-scaffold particles will serve as a surface for cell culture, and the sum of the surface areas of the micro-scaffolds will correspond to a culture area in plate culture.

In the micro-scaffold-adhering step, the cells are suspended in the medium, and the micro-scaffolds are also suspended so that the cells adhere to the micro-scaffolds. After cell adhesion, the micro-scaffolds having increased weight are precipitated and deposited on the bottom of the syringe.

The micro-scaffolds may be made of at least one selected from the group consisting of chitosan powder, alloderm (human dermis) powder, porous poyethylene powder, PTFE (polytetrafluoroethyelene) powder, PLGA (polylactic-co-glycolic acid) powder, PGA (polyglycolic acid) powder, PLA (lactic-co-glycolic acid) powder, PLLA (poly L-lactic acid) and PCL (poly e-carprolactone).

The proliferation step is a step of periodically performing a moving, shaking, stirring or blending process to separate saturated scaffold particles and to increase the possibility for the saturated scaffold particles to come into contact with fresh scaffold particles and to allow the cells to grow on the fresh scaffold particles. At a time point when the fresh scaffold particles are saturated, additional scaffolds are added while the moving process is performed such that the change of cell proliferation is maintained at a constant level.

This step is substituted for the prior process of separating connected cells from each other and dispersing and seeding the separated cells onto a fixed scaffold. Thus, this step eliminates a process of separating cells using a chemical substance (e.g., trypsin) to minimize the reduction in cell viability.

Also, in this step, the ratio of saturated scaffold particles is controlled to minimize the chance of contact inhibition caused by a rapid increase in cell density so as to the total amount of contact inhibition. Furthermore, the cell density capable of maintaining cell-to-cell signals most suitable for cell proliferation is maintained to maximize the total amount of cell proliferation signals.

A static precipitation state is a proliferation environment, which provides stable cell migration, because there is no change in the relative position of the scaffold particles. Thus, the static precipitation state should be maintained for more than a given time of period. In the moving or shaking period, some of cells are detached, and then adhere to fresh scaffold particles.

Scaffold particles having cells attached thereto are saturated within a short time so as to no longer grow. However, when scaffold particles connected thereto exist, cells will migrate to and proliferate on the surface of the connected particles having no contact inhibition, and when the surface of the connected particles is surrounded by cells, it reaches complete contact inhibition such that cells no longer can proliferate thereon. In this case, when the connected particles come into contact with fresh empty particles, some of the cells attached to the particles will migrate to and proliferate on the fresh particles.

Thus, the chance of cell proliferation is maximized by periodically shaking micro-scaffold particles to cause contact with fresh empty particles, and gradually increasing the amount of the micro-scaffolds through the addition of fresh scaffolds to maintain the density of empty scaffold particles. In this process, the scaffolds are added in small amounts at an initial stage, and then, added in exponential amounts. The addition of a small amount of the scaffolds at the initial stage is performed to maintain the scaffolds at suitable density, because, when saturated scaffolds are excessively spaced apart from other saturated particles, cell-to-cell signaling becomes difficult to weaken proliferation induction. Moreover, the size and shape of the scaffold particles should also be suitably maintained.

This concept is applied as a substitute for the prior process of separating and dispersing cells to control cell density in the concept of cell units. That is, this concept provides an effect similar to the control of density of cell units in terms of the maintenance of cell density by separating adjacent connected scaffold particles through a physical force caused by the moving force of the scaffold particles and dispersing the separated particles in the concept of scaffold particle units so as to control the density of the scaffold particles. For this reason, it is preferable to use micro-scaffolds having suitable size (20-100 mm).

In this concept, because each of scaffold particles saturated with a plurality of cells is regarded as a minimum unit, all processes are carried out in a state in which cells adhere to scaffold particles, and the separation between scaffold particles is more easily achieved compared to the separation between cells, which are not separated without a special chemical substance. In more principal terms, this concept applies a new fact that the inertia for scaffold particles having a plurality of cells attached thereto to move with the movement of liquid, that is, the inertia caused by the weight of scaffold particles, and the resistance of liquid such as medium, can become a physical force sufficient for the separation between cells, which connect the scaffold particles with each other.

Thus, the size of each of scaffold particles should be larger than a given size and the period of moving or shaking of scaffold particles should be suitable such that excessive connection of cells between the particles does not occur. Although these suitable values vary depending on the material of scaffolds and the kind of cells, the suitable ranges thereof can be determined through a simple experiment. For example, micro-scaffolds may have a size of 20-250 µm, the moving or shaking of the scaffolds can be carried out for 0.5-2 minutes at an interval of 4-8 hours, and the addition of fresh scaffolds can be performed by adding them at an interval of 16-48 hours in an amount 1.5-4 times as large as the amount just before the addition thereof. When cells are to be transplanted in vivo together with micro-scaffolds after culture, the micro-scaffolds preferably have a size of 20-100/an, which can be injected in vivo by an injection needle, and other factors, including the moving period and time of the micro-scaffolds, and the amount of fresh micro-scaffolds added, can be determined depending on the characteristics of cells through a pre-test.

The culture method according to the present invention can be constructed such that all steps, including fat extraction, pretreatment and culture steps, are performed in a closed syringe for fat extraction and culture.

In the syringe, the cylindrical body is the same as that of a general medical syringe, but the top of the body, to which a needle is generally attached, is centrally located, and a thread is formed on the outer surface of the body such that the body can be sealed with a rubber stopper. The plunger of the piston can be separated such that the piston can be mounted on a centrifuge, and a passage is formed in the piston such that the space in the syringe communicates with outside through the piston. Thus, the piston can be opened and closed, and liquids, such as a cell lysis, a wash buffer, a medium and a scaffold suspension, and gases, oxygen and carbon dioxide, can be injected and removed through the piston.

A thread is formed on the inner surface of the passage of the piston, such that one selected from among a plunger, a connecting tube and a stopper can be mounted in the passage. The piston hermetically seals the syringe throughout the culture process to minimize the possibility for medium to come into contact with external air during a movement or washing process and also minimize the possibility of contamination caused by the mistake of research staffs. Moreover, unlike a container opened at the upper end thereof, the syringe of the present invention is operated in easy and simple manner, because it can be shaken only by an operation of shaking or overturning the syringe without a separate stirrer or power.

The rubber stopper at the top of the body makes it possible to perform a sampling process with a syringe needle at any time to minimize operations and exposure, thus minimizing the possibility of contamination during the sampling process.

The syringe used in the present invention readily available and inexpensive and makes it possible to easily transfer cells from an extraction step in a surgical room to a culture place. Accordingly, the present invention is cost-effective, does not require complicated processes and various implements or expensive culture systems, and thus has a very great advantage of reducing cost, when various culture processes are simultaneously required as in stem cell studies.

The method for culturing cells using the syringe, comprises: a pretreatment step of extracting cells with a syringe, the piston of which can be opened and closed, and then centrifuging and washing the collected cells so as to be suitable for proliferation; a micro-scaffold-adhering step of opening the piston of the syringe, placing medium and micro-scaffolds into the syringe, adhering the cells to the micro-scaffolds in the medium in a suspended state, and precipitating and depositing the micro-scaffold-adhered cells onto the bottom of the syringe! a cell culture step of culturing the cells in a state in which the piston is opened; a proliferation step of, after a given time of cell culture, adding an additional medium and micro-scaffolds through the piston opening, and then subjecting the micro-scaffolds to a moving, shaking, rolling, stirring, whirling, rocking, mixing, blending or rotation process; and a proliferation-repeating step of periodically repeating the proliferation step.

In the above method, the extraction of cells is performed by removing a rubber stopper at the top of the syringe, coupling an injection needle for fat extraction to the top, blocking the passage of the piston in the syringe, attaching a suction cable to the plunger of the syringe, pricking the needle into a suction site and applying negative pressure to the back of the piston to suck and collect fat into the syringe.

The centrifugation and washing of the cells are performed by removing the needle from the syringe, sealing the top with the rubber stopper, adding collagenase through the passage of the piston, blocking the piston passage to seal the inner space of the syringe, placing the syringe in a centrifuge, centrifuging the content of the syringe, removing byproducts through the passage of the piston, introducing a wash buffer through the passage of the piston, shaking the syringe a few tens of times, and then removing the wash buffer.

The adhesion of the cells to the micro-scaffolds is performed by injecting medium and micro-scaffolds through the passage of the piston of the syringe, shaking the syringe 3-4 times to mix the contents of the syringe, and allowing the micro-scaffolds and the fat cells to be stably maintained in a state suspended in the medium such that the fat cells adhere to the micro-scaffolds and, at the same time, precipitate.

The cell culture and proliferation are performed by periodically shaking the syringe with a shaker in a state in which the piston is opened, adding additional medium and micro-scaffolds after completion of primary cell culture, and then periodically shaking the syringe.

The method for culturing cells using the syringe has the following advantages which are differentiated from the prior culture methods:

1) fat tissue can be separated, washed and centrifuged without the transfer of the fat tissue from the syringe to other containers;
2) the replacement of the supernatant medium is readily achieved even in a static state in which the scaffolds and the cells are precipitated;
3) aeration with intended gas can be easily maintained either by making aeration through the piston in an incubator filled with a specific gas or by injecting a specific gas through the piston and closing the piston;
4) medium can be easily replaced without shaking the scaffolds;
5) the processes of adding scaffolds and replacing medium and gas are easily performed;
6) centrifugation is easily performed;
7) stirring is easily achieved because the syringe can be turned over;
8) cell loss is minimized because one container is used;
9) infection is minimized due to a sealing process;
10) a process of separation between cells can be eliminated due to the use of micro-scaffolds;
11) the density of cells can be controlled at a desired level by controlling scaffolds during dilution, dispersion and seeding processes! and
12) a frozen cell sample stored together with scaffolds can be immediately used for proliferation without any separation process so as to maximize cell viability and reduce cost and time.

Advantageous Effects

Among prior culture methods for cell proliferation, in a method of three-dimensional Iy culturing cells using scaffolds, when cells proliferate, resulting in lack of a space in which cells can further proliferate, cell proliferation rate will be reduced due to contact inhibition. However, in the present invention, the number of cells can be greatly increased by maintaining proliferation rate through a process of dispersing cells in a new space, and allowing cells to continue to proliferate. For this dispersion of cells, connected adjacent cells should be separated from each other and separated from scaffolds, but in the prior art, this separation is performed using a chemical substance or enzyme such as trypsin.

This process of separation using a chemical substance or enzyme is a process of lysing some of cells and causes damage to cells. It is impossible to repeat this separation process more than a given number of times, because, it is considered that when a process of recovering cells from the damage is repeated, the possibility of gene mutation will be increased. However, the present invention allows this cell separation process to be eliminated, and thus allows cells to proliferate infinitely without the limitation of number of cell divisions. Moreover, the prior culture methods require a considerable amount of time and effort for enzyme action, centrifugation, re-seeding, recovery from cell damage, and the like, resulting in a great reduction in proliferation rate, but the present invention can spare this time and effort, and thus show a significantly high proliferation rate compared to the prior methods.

Equipment for use in cell culture necessarily requires systems for minimizing the chance of contact with bacteria in air, requires quantitative instruments and containers allowing a suitable amount of material, and should be provided with containers to be used in centrifugation conducted at any time, and transfer means. However, because such systems are frequently contaminated with bacteria, due to the hands or gloves of researchers, insufficiently disinfected containers, and the introduction of non-purified air, the minimization of contamination possibility through thorough checking and repeated learning is necessary in all research institutes. However, in the present invention, the above-described syringe (syringe for fat extraction and culture, which is opened in the front thereof and has an inlet to which a rubber stopper or a valve is attached) is used instead of a general experimental conical tube (Falcon tube (B-D Co.)) as a culture container. Accordingly, a culture process can be performed in a space closed to the maximum, so as to reduce the chance of contamination, and thus investment in equipment and the training of research staffs can be reduced.

BEST MODE

Figure 1:
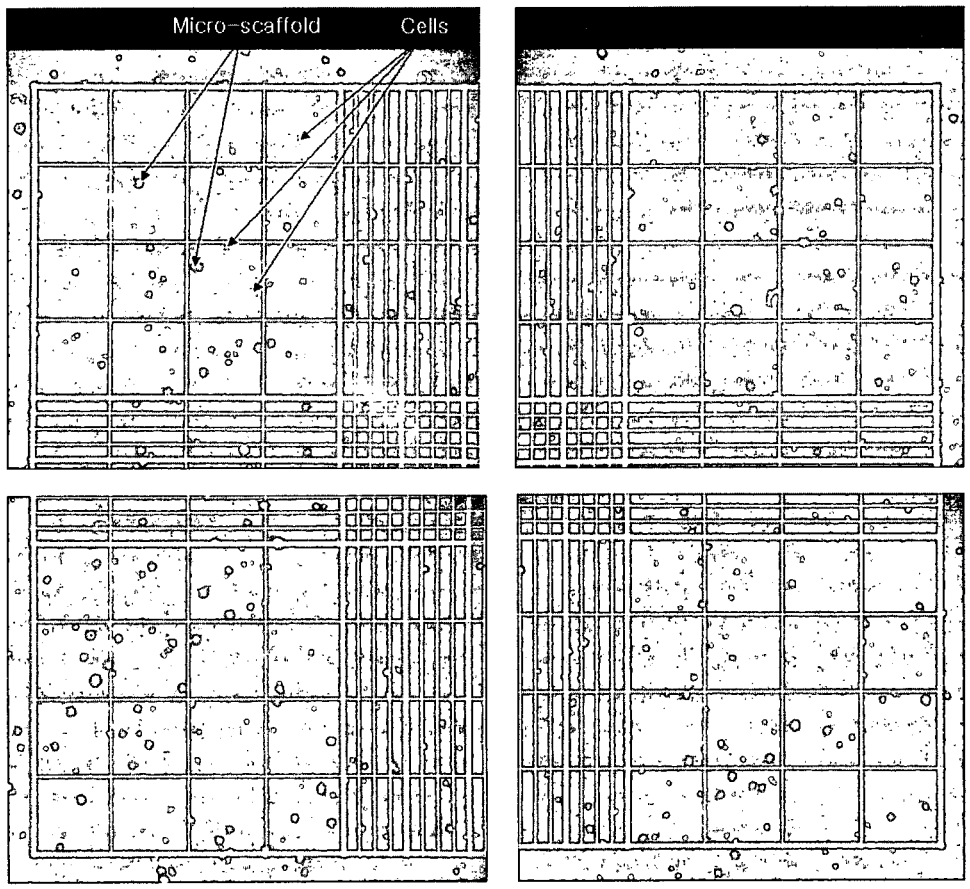
FIG. 1 is a photograph showing a result of haemocytomer measurement of control group 1 (static culture).

Hereinafter, the present invention will be described in further detail with reference to examples of cell culture.

The following examples were performed to examine the effects of intermittent shaking (or moving status, rolling, stirring, whirling, rocking, mixing, rotation, etc.) and the gradual addition of micro-scaffolds (micro-beads) on cell culture efficiency in three-dimensional cell culture processes, which were carried out using the same amount of micro-scaffolds (micro-beads) and the same amount of cells. Also, the examples were performed to confirm whether the following hypotheses would be realized.

Hypothesis 1

An attempt to suitably maintain two conditions required for cell proliferation, that is, 1) proliferation-inducing signals between cells and 2) proliferation-inhibitory signals between cells, will act as a method capable of increasing cell proliferation.

Hypothesis 1-1

In comparison with 1) "static non-shaking", intermittent shaking allows a given distance between cells to be maintained for a given time to maximize proliferation-inducing signals. Also, when contact inhibition starts to become strong, intermittent shaking allows cells to be separated from each other to reduce contact inhibition, and thus it involves a static status compared to 2) "continuous shaking (or stirring, rolling, rocking, whirling, etc.)". Accordingly, intermittent shaking will increase cell proliferation compared to the static non-shaking 1) and the continuous shaking 2) by further increasing a proliferation-inducing effect through a partial increase in cell density and minimizing contact inhibition.

Hypothesis 1-2

The gradual addition of scaffolds is performed to minimize the increase in the relative concentration of cells resulting from the increase in the number of cells in the proliferation of the same amount of cells, that is, to minimize contact inhibition. The concept thereof is that cells are first seeded onto a small amount of scaffolds at an initial stage and the amount of scaffolds is increased slowly. In order to prevent proliferation-inducing signals from becoming weak due to a low relative concentration of cells caused by seeding cells onto a large amount of scaffolds at an initial stage, the relative concentration of cells is maintained at a high level in the initial stage. Then, the relative concentration of cells is maintained at a constant level in order to minimize proliferation inhibitory signals, which will be increased due to the increase in the relative concentration of cells, caused by the proliferation of cells. This gradual addition of scaffolds will ultimately contribute to increase the proliferation of cells.

Hypothesis 2

In three-dimensional cell proliferation with micro-scaffolds, connected cells will be divided between the scaffold particles only by simple shaking or stirring. Thus, there will be no need to use a mutation-inducible substance such as trypsin for cell division for the re-seeding of cells.

Hypothesis 3

When the hypotheses 1-1 and 1-2 are combined with the hypothesis 2 (test group 2), the proliferation of cells will be increased due to the synergic effect of the hypothesis 2, compared to culture methods which apply such hypotheses, that is, "static status" (control group 1; 1-1-2), "continuous shaking (control group 2; 1-1-2), or test group 1 (intermittent shaking) which applies only the hypothesis 1-1.

To confirm such hypotheses, the following tests were performed.

[Material and Method]

Micro-scaffolds: PLLA (10-100 μm diameter; spherical; nonporous);

Cells: non-subcultured (PO) stromal cells extracted from fat tissue;

Media-' DMEM (containing 4.00 mM L-glutamine, 4500 mg/L glucose, with sodium pyruvate, DW-0.2 μm sterile filtered)+10% FBS+1% PS;

Wash buffer: PBS (containing KCl: 200.00 mg/L, $KH_2PO_4$: 200.00 mg/L, NaCl: 8000.00 mg/L, and $Na_2HPO_4H_2O$: 2160.00 mg/L);

Culture container: a 50-cc closed syringe for fat extraction and culture (Medican Co., Ltd.) (positioned upright→induction of precipitation of cells and micro-scaffold);

Shaker: Vortex Genie-2 (Scientific industries Co.)-60 rpm;

Culture temperature and environment: 37° C. and 5% CO2-incubator; and

Total culture period: 7 days.

[Culture Method]

1) Fat was extracted from fat tissue with a needle inserted into a closed syringe for fat extraction and culture.

2) Then, the needle of the syringe was removed, the top of the syringe was blocked with a rubber stopper, collagenase is introduced through the passage of the piston, and the piston passage was blocked to close the inner space of the syringe.

3) Then, the syringe was placed in a medical centrifuge and the content thereof was centrifuged. Then, the content was separated into top byproducts and bottom fat cells, and the top byproducts were discharged to the outside through the piston passage, thus obtaining fat cells.

Then, a wash buffer (PBS) was introduced through the piston passage into the syringe, and the syringe was uniformly shaken to wash the fat cells. Then, the wash buffer was removed by suction through the piston passage. In this way, pretreated stromal cells are obtained.

4) Then, the pretreated cells were added to media and micro-scaffolds, and attached to the micro-scaffolds in a state suspended in the medium. The cells were cultured in the specified conditions.

In all groups, including control groups and test groups, 25 μi of a sample was taken from the central portion of each culture medium after one minute of shaking after 7 days of culture.

a) Control Group 1

In static culture, 8 ml of scaffolds were allowed to precipitate in 40 cc of medium for more than one hour, and then cells were seeded at a density of $1×10^6$ cell/ml onto the medium through a pipette.

b) Control Group 2

In continuous shaking culture, the same process as in the control group was carried out, followed by continuous shaking.

c) Test Group 1

In intermittent shaking culture, the same process as in the control group 1 was carried out, followed by shaking for 1 minute at a 6-hr interval.

d) Test Group 2

In culture comprising intermittent shaking+gradual addition of micro-scaffolds, 500 μl of micro-scaffolds were added to 40 cc of medium and shaken. Then, the medium was shaken for 1 minute at a 6-hr interval.

After 24 hours (1 day), 500 μi of micro-scaffolds were added to the culture medium and shaken. Then, the medium was shaken for 1 minute at a 6-hr interval.

After 36 hours (2 days), 1 ml of micro-scaffolds were added to the culture medium and shaken, followed by shaking for 1 minute at a 6-hr interval.

After 72 hours (3 days), 2 ml of micro-scaffolds were added to the culture medium and shaken, followed by shaking for 1 minute at a 6-hr interval.

5 days after the start of culture, 4 ml of micro-scaffolds were added to the culture medium and shaken, followed by shaking for 1 minute at a 6-hr interval.

[Measurement Method]

1) Sample Extraction

25 μi of a sample was extracted from the central portion of each of the culture media immediately after shaking, and 10 μl of a sample for cell counting was extracted from each of the samples.

Then, at 1 day, 2 days, 3 days, 4 days and 7 days after the start of static and shaking culture, 25 μi of micro-scaffolds were sampled and incubated in an incubator (37° C. and 5% $CO_2$) with trypsin-EDTA for 10 minutes. Then, the sampled micro-scaffolds were taken out, and to inactivate trypsin-EDTA, DMEM medium (10% FBS+1% PS) is added the micro-scaffolds, followed by shaking for 1 minute. Then, the micro-scaffolds were stained with trypan blue, and cells on the micro-scaffolds were counted with a haemocytomer.

Control group 1 was applied only in the last sampling and measured for cell number using a haemocytomer. The remaining sample was used for staining.

b) Cell Counting by Microscopic Examination and Staining Method

Cells were visually counted with a haemocytomer under a microscope.

c) H&E Staining

The micro-scaffolds were stained with haematoxylin & eosin, and cells attached to the micro-scaffolds were examined.

d) DAPI Staining

The micro-scaffolds were stained with DAPI solution, and cells attached to the micro-scaffolds were examined using fluorescent microscopy.

All the groups except for control group 1 were sampled after 1 minute of shaking at 1 day, 2 days, 3 days, 5 days and 7 days, and the samples were measured.

[Test Results]

1) Control Group 1 (Static Culture)

Cell total number: 220 micro scaffolds: $220×10^4×4×¼=2.2×1( )^6$

2) Control Group (Continuous Shaking Culture)

Cell total number: 260 micro-scaffolds: $260×1( )^4× 4×¼=2.6×K)^6$

3) Test Group 1 (Intermittent Shaking Culture)

Cell total number: 340 micro-scaffolds: $340×10^4×4×¼=3.4×1( )^6$

4) Test Group 2 (Culture Comprising Intermittent Shaking+Gradual Addition of Micro-Scaffolds)

Cell total number: 680 micro-scaffolds: $680×10^4×4×¼=6.8×1( )^6$

[Calculation of Doubling Time]

To calculate the doubling time for cells to proliferate two times, 25 μZ of a sample was taken at a 6-hr interval, and 10 μZ thereof was measured for cell number. The measurement results are shown in Table 1 below.

TABLE 1

| | Time | | | | | | | |
|---|---|---|---|---|---|---|---|---|
| | 0 | 6 | 12 | 18 | 24 | 30 | 36 | 42 |
| Control group 1 | 100 | 114 | 127 | 139 | 149 | 158 | 177 | 205 |
| Control group 2 | 100 | 117 | 131 | 148 | 159 | 168 | 185 | 209 |
| Test group 1 | 100 | 120 | 133 | 150 | 168 | 211 | | |
| Test group 2 | 100 | 123 | 142 | 167 | 225 | | | |

Equation for calculation: ln(Nf/Ni)/ln 2, wherein Nf: the number of extracted cells per hour, and Ni: the number of initial cells 1) Control Group 1 (Static Culture)
doubling time: about 40 hours (including dead cells).
2) Control Group 2 (Continuous Shaking Culture)
doubling time: about 40 hours.
3) Test Group 1 (Intermittent Shaking Culture)
doubling time-' about 28 hours.
4) Test Group 2 (Culture Comprising Intermittent Shaking+Gradual Addition of Micro-Scaffolds)
doubling time: about 20 hours.

Then, each of the control and test groups was photographed.

Figure 2:
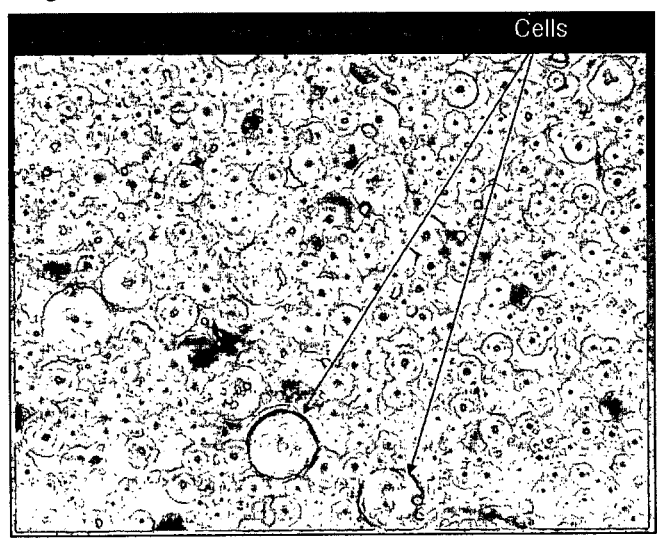
FIG. 2 is a photograph showing a result of H&E x20 of the control group 1 (static culture).
Figure 3:
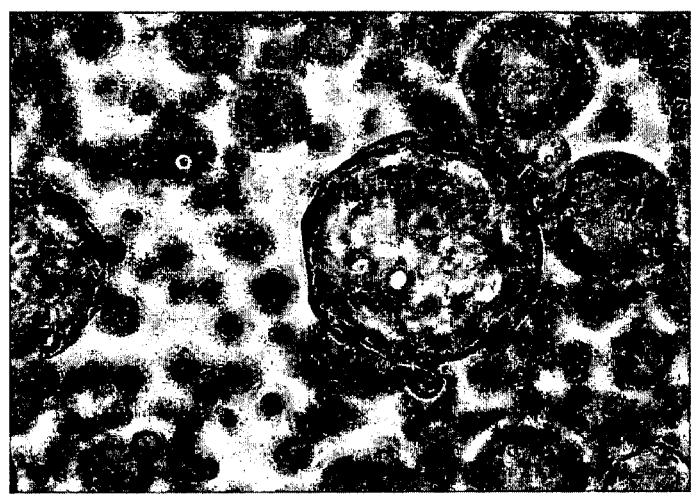
FIG. 3 is a photograph showing a result of H&E x40 of the control group 1 (static culture).
Figure 4:
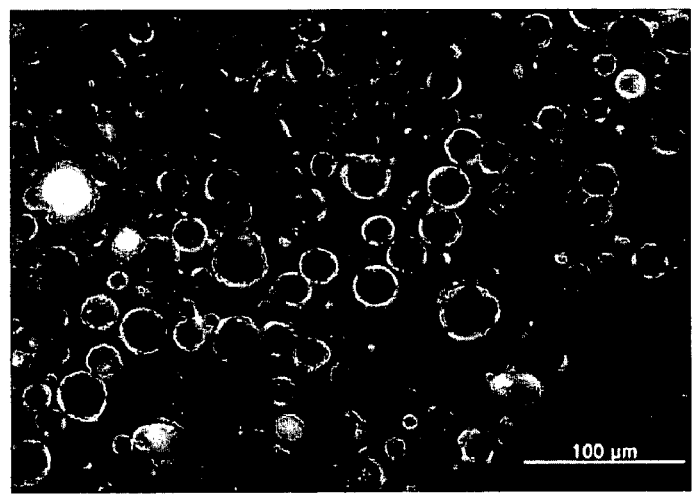
FIG. 4 is a photograph showing a result of DAPI staining x20 of the control group 1 (static culture).
Figure 5:
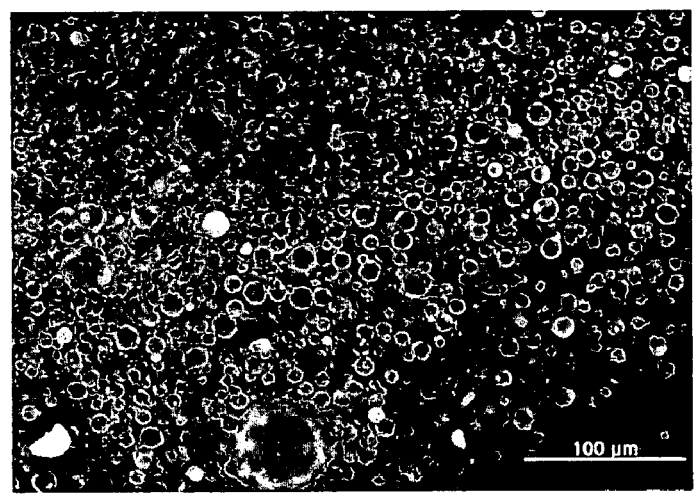
FIG. 5 is a photograph showing a result of DAPI staining x10 of the control group 1 (static culture).

1) Control Group 1 (Static Culture; $2.2 \times 10^6$ Cells)
FIGS. 1 to 5 show the results of (1) haemocytomer measurement, (2) H&E x20, (3) H&E x40, (4) DAPI staining x20 and (5) DAPI staining x10 of the control group, respectively.

Figure 6:
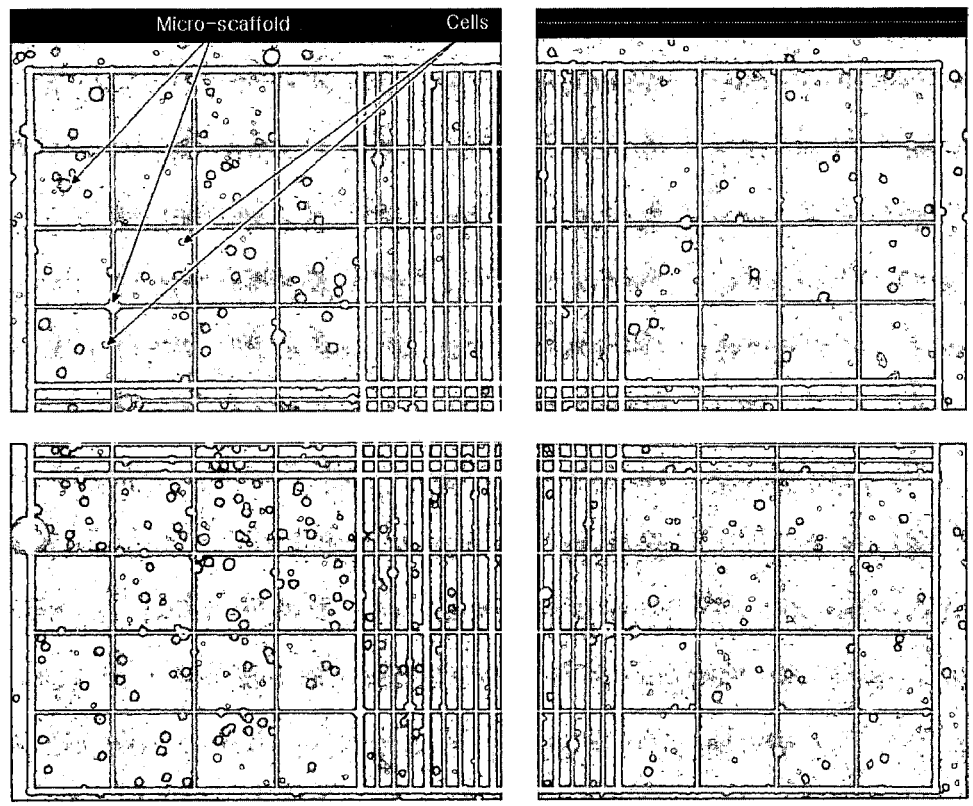
FIG. 6 is a photograph showing a result of haemocytomer measurement of control group 2 (continuous shaking culture).
Figure 7:
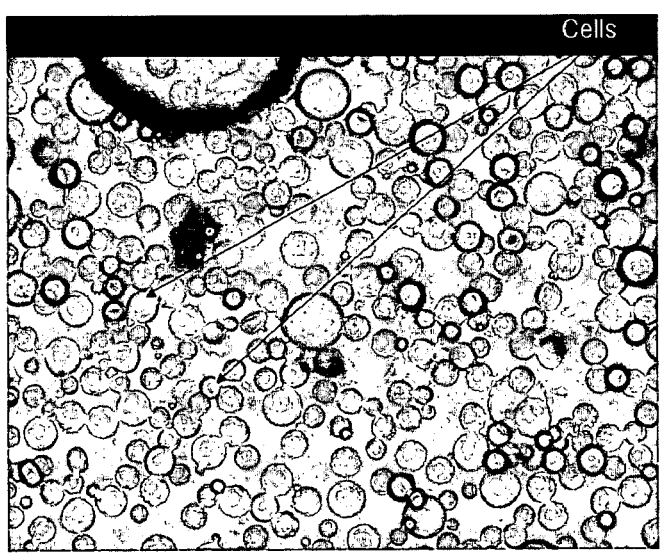
FIG. 7 is a photograph showing a result of H&E x40-1 of the control group 2 (continuous shaking culture).
Figure 8:
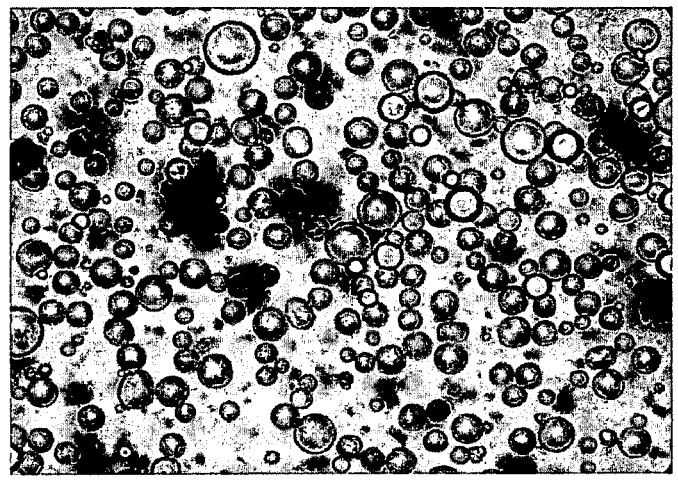
FIG. 8 is a photograph showing a result of H&E x40-2 of the control group 2 (continuous shaking culture.
Figure 9:
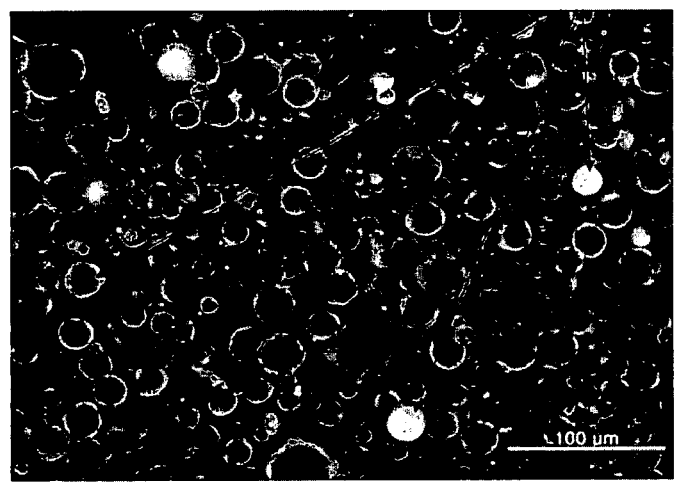
FIG. 9 is a photograph showing a result of DAPI staining x20-1 of the control group 2 (continuous shaking culture).
Figure 10:
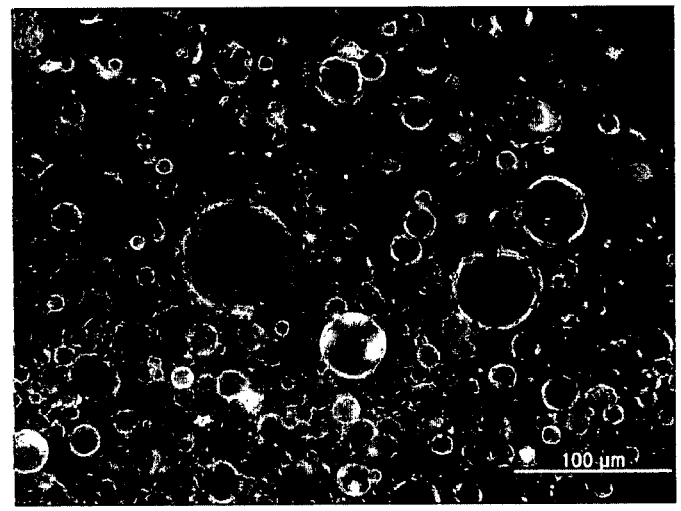
FIG. 10 is a photograph showing a result of DAPI staining x20-2 of the control group 2 (continuous shaking culture).

2) Control Group 2 (Continuous Shaking Culture! $2.6 \times 10^6$ Cells)
FIGS. 6 to 10 are photographs showing the results of (6) haemocytomer measurement, (7) H&E x40-1, (8) H&E x40-2, (9) DAPI staining x20-1 and (10) DAPI staining x20-2 of the control group 2, respectively.

Figure 11:
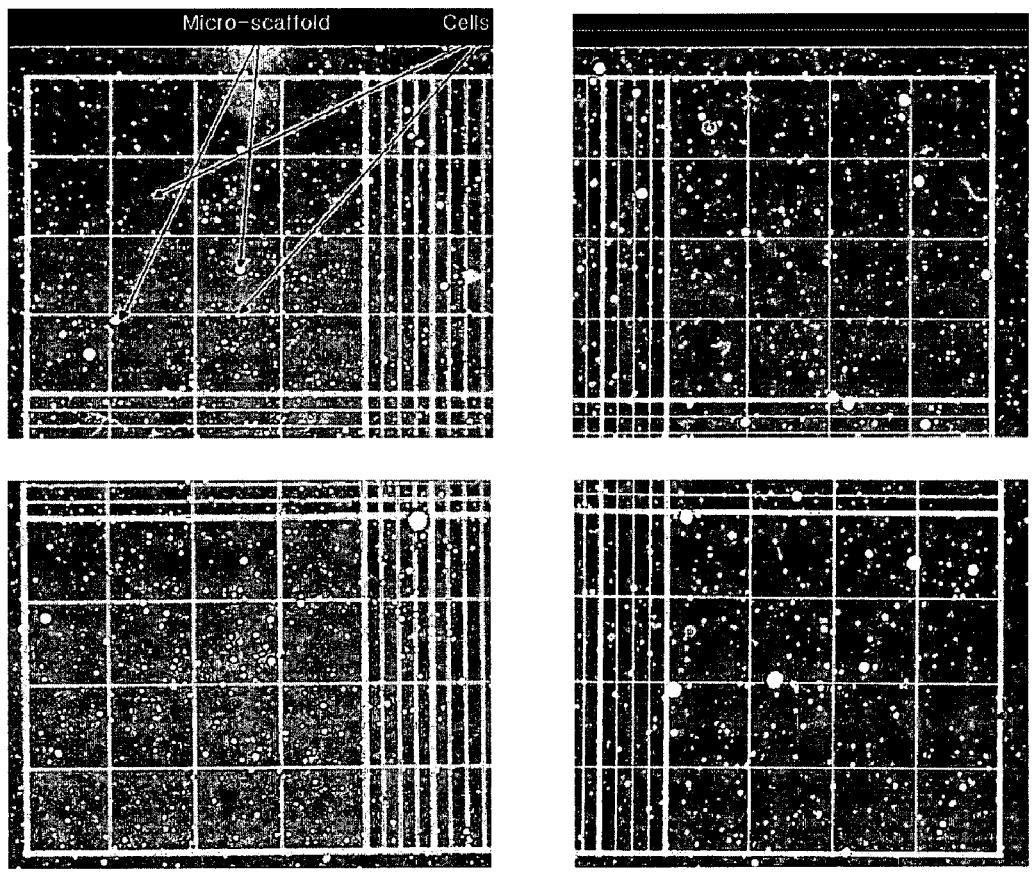
FIG. 11 is a photograph showing a result of haemocytomer measurement of test group 1 (intermittent shaking culture).
Figure 12:
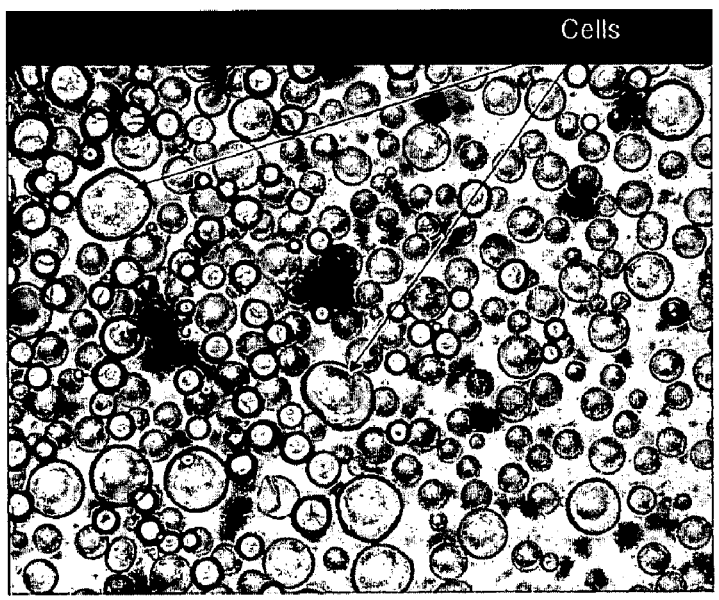
FIG. 12 is a photograph showing a result of H&E x40-1 of the test group 1 (intermittent shaking culture).
Figure 13:
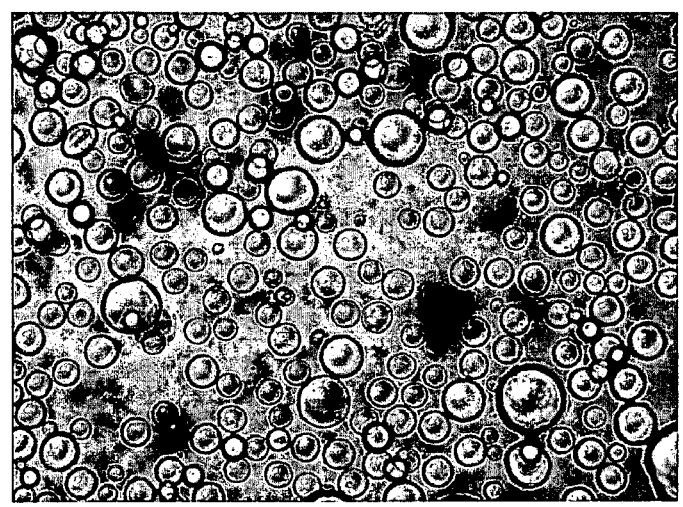
FIG. 13 is a photograph showing a result of H&E x40-2 the test group 1 (intermittent shaking culture).
Figure 14:
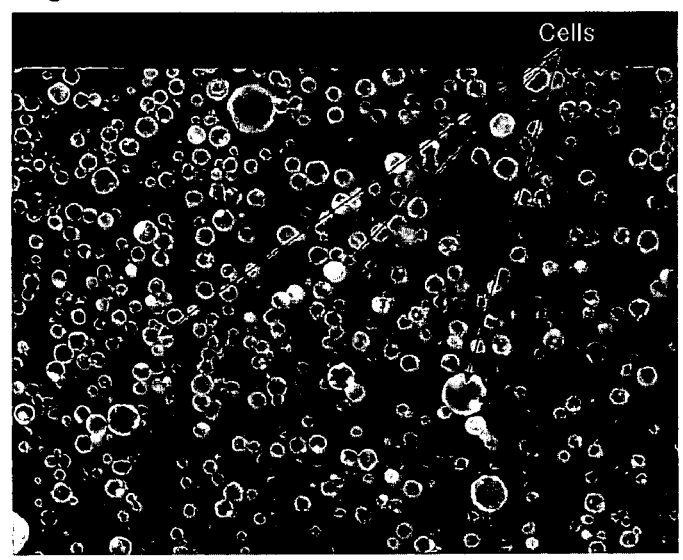
FIG. 14 is a photograph showing a result of DAPI staining x10 of the test group 1 (intermittent shaking culture).
Figure 15:
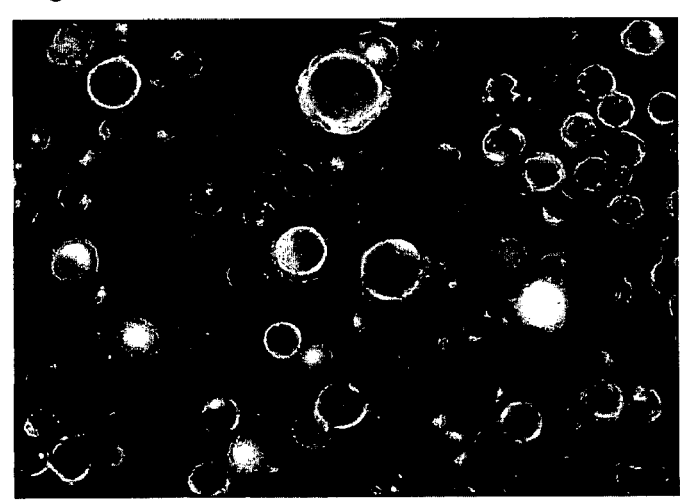
FIG. 15 is a photograph showing a result of DAPI staining x20 of the test group 1 (intermittent shaking culture).

3) Test Group 1 (Intermittent Shaking Culture; $3.4 \times 10^6$ Cells)
FIGS. 11 to 15 are photographs showing the results of (11) haemocytomer measurement, (12) H&E x40-1, (13) H&E x40-2, (14) DAPI staining x10 and (15) DAPI staining x20 of the test group 1, respectively.

Figure 16:
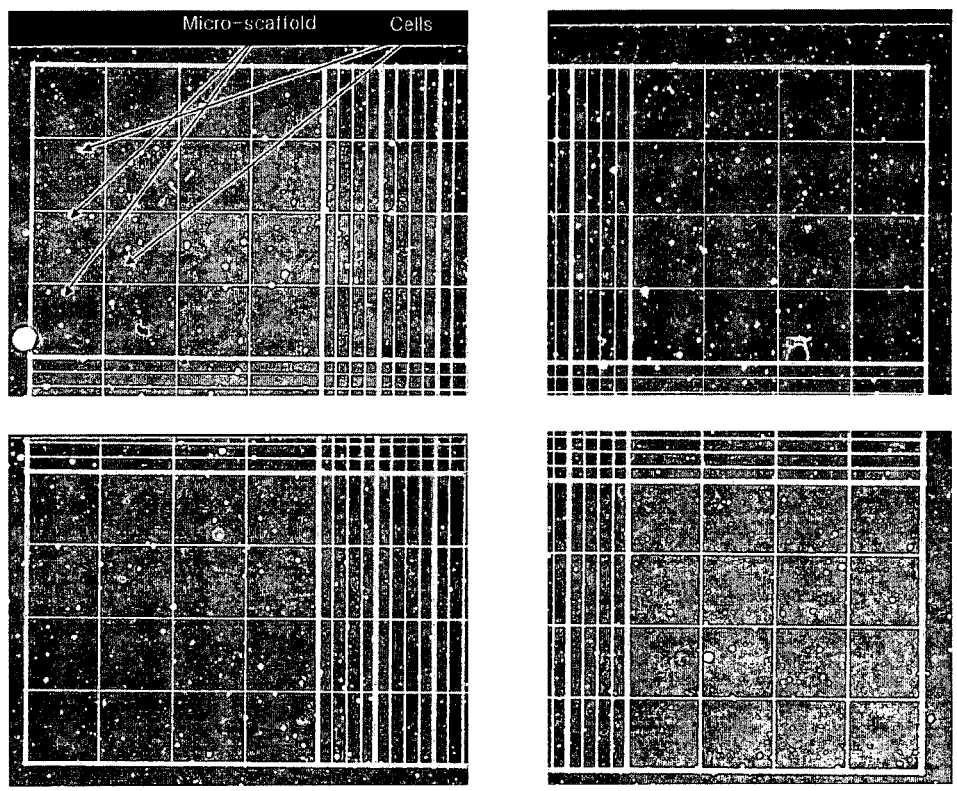
FIG. 16 is a photograph showing a result of haemocytomer measurement of test group 2 (culture comprising intermittent shaking+gradual addition of micro-scaffolds).
Figure 17:
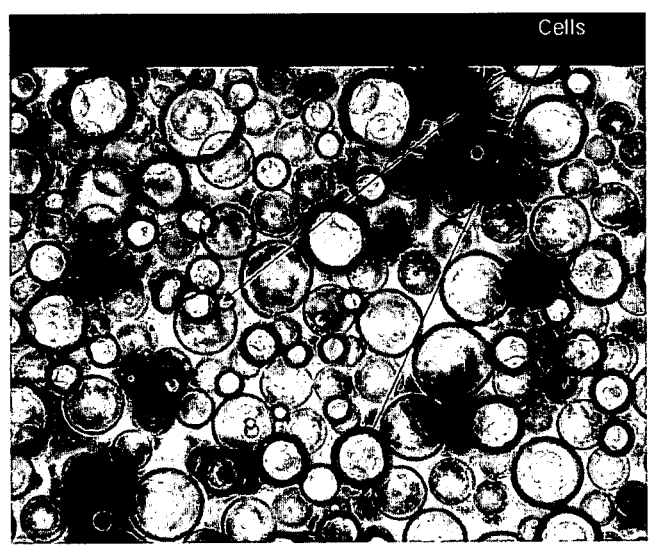
FIG. 17 is a photograph showing a result of H&E x40-1 of the test group 2 (culture comprising intermittent shaking+ gradual addition of micro-scaffolds).
Figure 18:
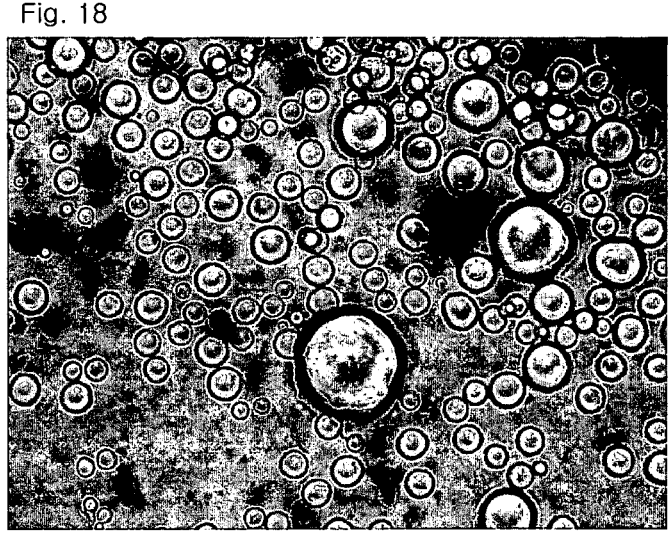
FIG. 18 is a photograph showing a result of H&E x40-2 of the test group 2 (culture comprising intermittent shaking+ gradual addition of micro-scaffolds).
Figure 19:
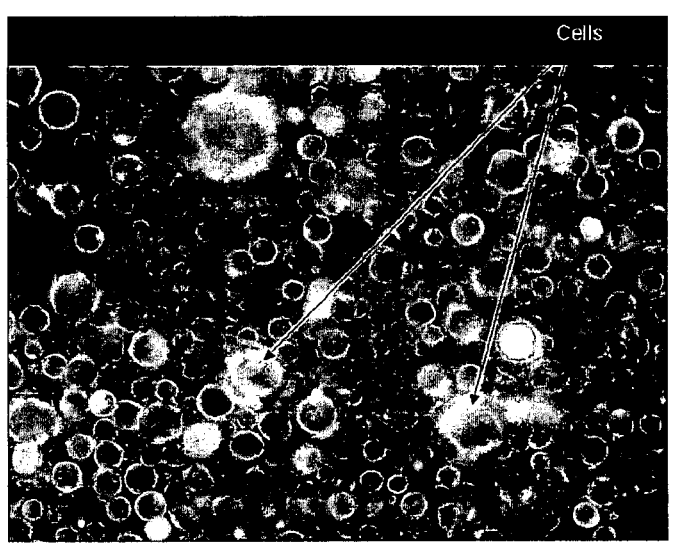
FIG. 19 is a photograph showing a result of DAPI staining x10 of the test group 2 (culture comprising intermittent shaking+gradual addition of micro-scaffolds).
Figure 20:
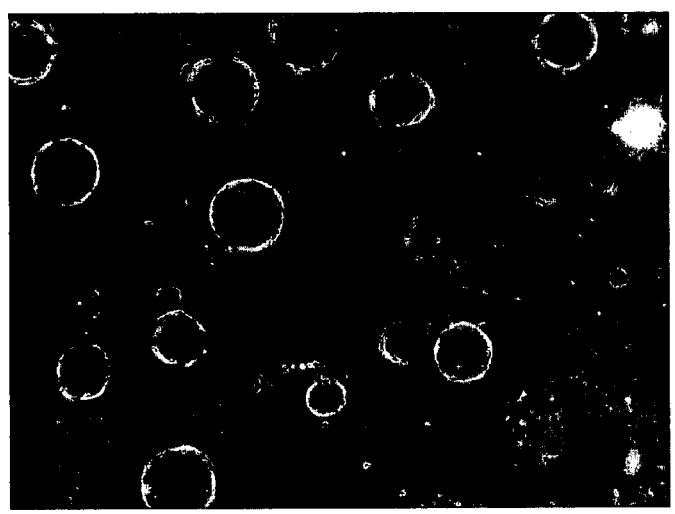
FIG. 20 is a photograph showing a result of DAPI staining x20 of the test group 2 (culture comprising intermittent shaking+gradual addition of micro-scaffolds).

4) Test Group 2 (Culture Comprising Intermittent Shaking+Gradual Addition of Micro-Scaffolds; $6.8 \times 10^6$ Cells)
FIGS. 16 to 20 are photographs showing the results of (16) haemocytomer measurement, (17) H&E x40-1, (18) H&E x40-2, (19) DAPI staining x10 and (20) DAPI staining x20 of the test group 2, respectively.

From the above test results, it could be seen that the hypothesis (an attempt to suitably maintain two conditions required for cell proliferation, that is, 1) proliferation-inducing signals between cells and 2) proliferation-inhibitory signals between cells, will act as a method capable of increasing cell proliferation) was realized.

Moreover, the hypothesis 1-1 (In comparison with "static non-shaking" 1), intermittent shaking allows a given distance between cells to be maintained for a given time to maximize proliferation-inducing signals. Also, when contact inhibition starts to become strong, intermittent shaking allows cells to be separated from each other to reduce contact inhibition, and thus it involves a static status compared to "continuous shaking (or stirring, rolling, rocking, whirling, etc.)" 2). Accordingly, intermittent shaking will increase cell proliferation compared to the static non-shaking 1) and the continuous shaking 2) by further increasing a proliferation-inducing effect through a partial increase in cell density and minimizing contact inhibition) was realized.

Furthermore, the hypothesis 1-2 (The gradual addition of scaffolds is performed to minimize the increase in the relative concentration of cells resulting from the increase in the number of cells in the proliferation of the same amount of cells, that is, to minimize contact inhibition. The concept thereof is that cells are first seeded onto a small amount of scaffolds at an initial stage and the amount of scaffolds is increased slowly. In order to prevent proliferation-inducing signals from becoming weak due to a low relative concentration of cells caused by seeding cells onto a large amount of scaffolds at an initial stage, the relative concentration of cells is maintained at a high level in the initial stage. Then, the relative concentration of cells is maintained at a constant level in order to minimize proliferation inhibitory signals, which will be increased due to the increase in the relative concentration of cells, caused by the proliferation of cells. This gradual addition of scaffolds will ultimately contribute to increase the proliferation of cells) was also realized. In addition, the hypothesis 2 (In three-dimensional cell proliferation with micro-scaffolds, connected cells will be divided between the scaffold particles only by simple shaking or stirring. Thus, there will be no need to use a mutation-inducible substance such as trypsin for cell division for the re-seeding of cells) was also realized.

Moreover, the method, comprising intermittent shaking the gradual addition of micro-scaffolds, has an increased effect on cell proliferation compared to either the method comprising only intermittent shaking or the method comprising the gradual addition of micro-scaffolds.

INDUSTRIAL APPLICABILITY

As described above, the present invention provides a three-dimensional cell culture method for increasing cell proliferation efficiency by suitably regulating the proliferation-inducing and proliferation-inhibitory signals between cells, which are the greatest variables in proliferation efficiency.

The present invention can increase cell proliferation efficiency using a method comprising: properly using an environment where cell proliferation is accelerated by cell-to-cell signals or interactions; minimizing the phenomenon that, when proliferated cells adhere to each other, proliferation inhibitory signals will increase to reduce the relative ratio of an area where cells can proliferate; and performing intercellular separation at a suitable point of time using a physical force instead of using a chemical method, which is known to have a possibility of causing gene mutation.

In addition, the present invention suggests a cell culture method, which can reduce the economic burden required for experiments by simplifying complicated culture processes and various systems and instruments, makes it possible to achieve advanced studies even in small-scale systems, and enables reliable research results to be obtained.

The invention claimed is:

1. A method for three-dimensionally culturing cells using micro-scaffolds wherein the micro-scaffolds have surface areas allowing for the adhesion and proliferation of the cells, wherein the method is performed in a syringe wherein the syringe has a structure in which the top and inlet of the syringe can be blocked and the piston of the syringe is provided with a passage which can be opened and closed, the method comprising:

a) a pretreatment step of centrifuging and washing cells collected in the syringe so as to be suitable for proliferation;

b) a micro-scaffold-adhering step of placing medium and micro-scaffolds into the syringe with the collected cells, adhering the cells and micro-scaffolds to each other in a state suspended in the medium;
c) a cell culture step of culturing the cells in the syringe;
d) a micro-scaffold-gradual addition step of gradually adding micro-scaffolds, in which a small amount of the micro-scaffolds are used in an initial stage and the amount of the micro-scaffolds is then increased according to cell proliferation rate so as to maintain a suitable distance between the cells;
e) a periodic shaking step of periodically shaking, in which shaking is performed in order to separate connected cells from each other, after the cells are incubated for more than a given period of time;
and wherein one or both of steps d) and e) are performed repeatedly so as to regulate proliferation-inducing and proliferation-inhibitory signal between the cells.

* * * * *